United States Patent [19]

Layher

[11] Patent Number: 5,313,841

[45] Date of Patent: May 24, 1994

[54] DIE ADHESION TESTING METHOD AND APPARATUS

[75] Inventor: Francis W. Layher, San Diego, Calif.

[73] Assignee: Quantum Materials, Inc., San Diego, Calif.

[21] Appl. No.: 911,176

[22] Filed: Jul. 9, 1992

[51] Int. Cl.⁵ .............................................. G01N 3/08
[52] U.S. Cl. ........................................ 73/827; 73/856
[58] Field of Search ............... 73/827, 860, 150 A, 73/842, 856; 257/48

[56] References Cited

U.S. PATENT DOCUMENTS 3,107,524 10/1963 O'Connor .......................... 73/860
4,541,287 9/1985 Roper ............................ 73/856 X Primary Examiner—Jerry W. Myracle
Attorney, Agent, or Firm—Baker, Maxham, Jester & Meador

[57] ABSTRACT

A connector assembly for connecting to a chip and a substrate for testing the bond between a chip and a substrate in a testing apparatus, the connector assembly comprises a pair of connector blocks, each block having a generally square planar connecting face for bonding to oppositely directed faces of a chip and substrate, and a coupling end for mounting in a tensile testing machine, and a swivel connector assembly for connecting to the coupling and mounting in a tensile testing machine for the application of aligned tension to the chip and substrate.

20 Claims, 1 Drawing Sheet

U.S. Patent  May 24, 1994  5,313,841
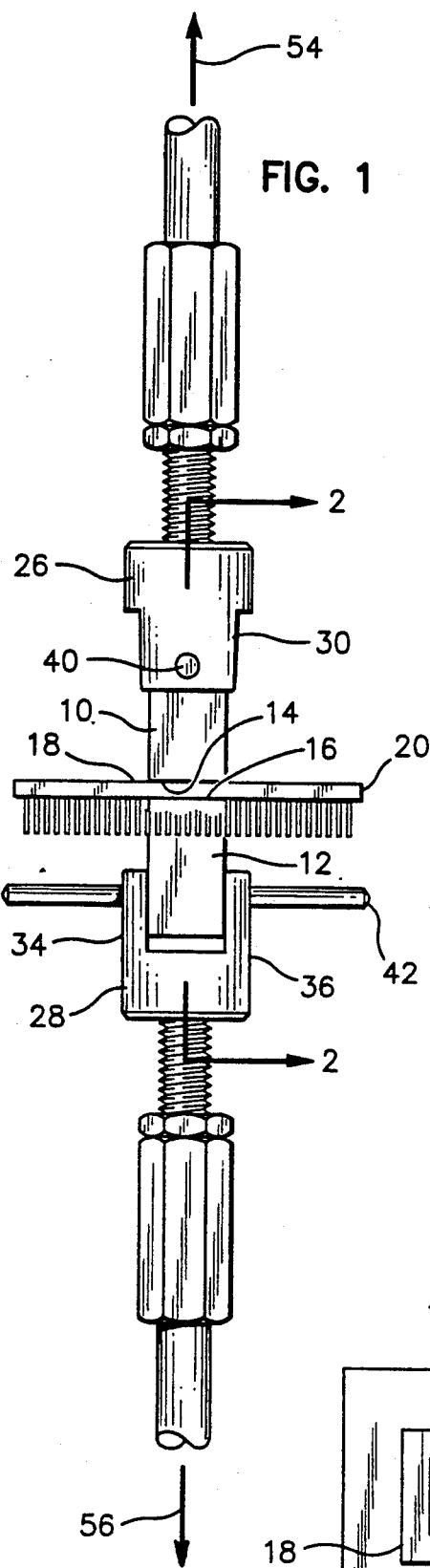
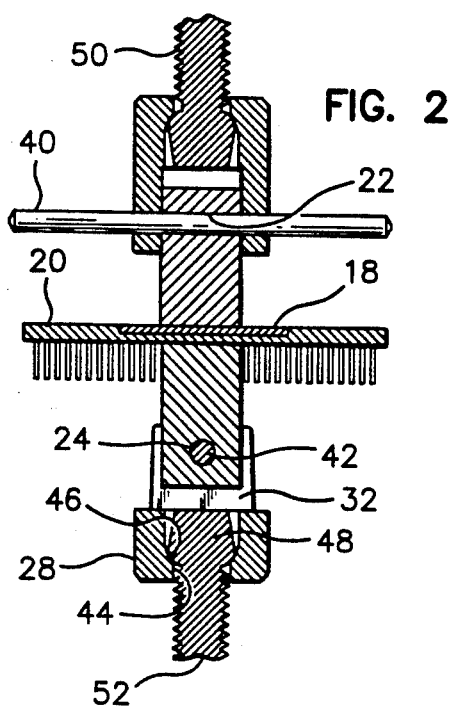
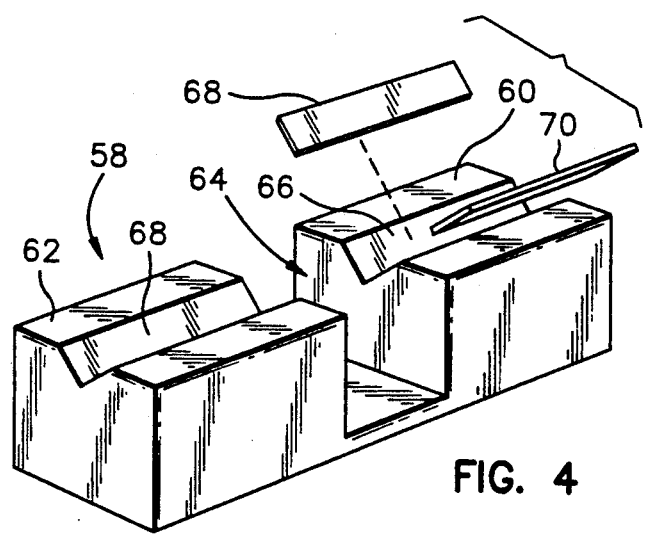
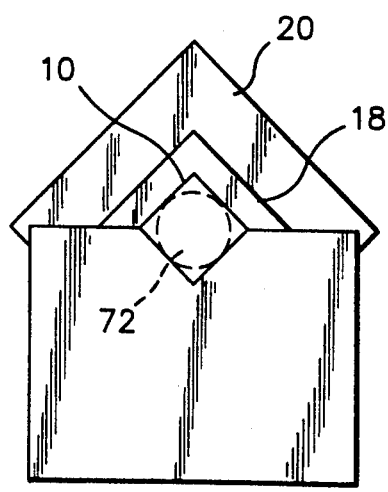
FIG. 1
FIG. 2
FIG. 3
FIG. 4
FIG. 5

DIE ADHESION TESTING METHOD AND APPARATUS

BACKGROUND OF THE INVENTION

The present invention relates to the art of semiconductor packaging, and more particularly to methods and apparatus for testing the bonding of surfaces in the art of packaging semiconductor devices.

Semiconductor chips or dies are packaged to tie the circuits thereof to the outside world. The chip is normally bonded to a substrate, such as ceramic in the process of packaging. Adhesive pastes have been used to secure heat sinks to ceramic semiconductor packages. In addition, metallic-glass pastes have been used for attaching semiconductor chips to ceramic substrates in the manufacture of semiconductor devices, and particularly, large scale integrated (LSI) and very large scale (VLSI) circuits.

These circuits typically include a semiconductor chip or die, e.g., silicon, gallium arsenide, etc., which is bonded to a supporting ceramic substrate. Commonly assigned U.S. Pat. Nos. 4,636,254, 4,761,224 and 4,968,738 are directed to improved silver-glass die attach pastes for the attachment of a semiconductor die to a ceramic substrate. These patents disclose silver-glass die attach pastes consisting generally of a mixture of silver flake and glass frit distributed in an organic vehicle, including a suitable organic resin and a suitable organic solvent.

To form a bond between a semiconductor die and a ceramic wafer or substrate, a selected quantity of the silver-glass paste is placed between the opposing die and substrate surfaces in a sandwiched relationship. The sample is dried and fired in a oven or furnace at temperatures above the glass transition temperature ($T_g$) of the glass constituent. During the drying and firing stages, the organic vehicle volatilizes and the glass flows to wet the ceramic substrate and die, while the silver flake sinters together. Upon cooling, the result is a secure bond between the die and the substrate.

One critical aspect of the semiconductor die/ceramic substrate bonding process is that the post-fired adhesive film must have an adequate bond strength to accommodate differential thermal expansion. If the bond line thickness is sufficient, the resultant bond will exhibit good resistance to differential thermal expansion rates between the die and substrate and will produce a bond having a high tensile strength. Interfacial stress that arises from a thermal mismatch between the die and substrate is directly proportional to both the area of attachment and the modulus of elasticity of the bonding adhesive. This stress is also inversely proportional to the bond line thickness. Since the modulus of elasticity for a given die attach adhesive is fixed, the only avenue available to reduce interfacial stress is to maintain a sufficient bond line thickness on each part assembled. For the proper bonding of silicon die to ceramic substrates, the bond line thickness must be increased proportionally to the area of the surfaces to be bonded.

A major aspect of the quality control of such packaging is adequate and reliable testing to insure uniform and adequate bond strength. The prior art method of testing is carried out by bonding studs to the face of the chip and to the face of the substrate by means of an epoxy that is cured in an oven. One common form of the studs have a configuration similar to that of a nail, with a flat head and with a blunt point. An extender plate is sometimes used between the head and chip where the chip is considerably larger than the stud head.

Another form of device is like a bolt with a threaded shank. The head of the studs are bonded to the chip and substrate. The shank of the studs are either screwed or clamped in tensile test stand and a force applied to separate the chip from the substrate. This is intended to give a measure of the strength of the bond.

A major problem with the prior art approach is that the studs may not be bonded precisely perpendicular to the surface of the chip and/or the studs may not be aligned. This results in a peel test rather than a true tensile test. Therefore, this method is not always accurate. For example, in some instances, it is found that the chip is peeled from substrate because of the lines of force. Thus, a true tensile strength is not measured.

Accordingly, it is desirable that an improved adhesion tensile strength testing apparatus and method be available.

SUMMARY OF THE INVENTION

It is therefore the primary object of the present invention to provide an improved adhesive tensile strength testing method and apparatus.

In accordance with a primary aspects of the invention, a chip to substrate bonding adhesive testing device includes coupling blocks for direct attachment to chip and to a substrate, with an alignment jig to assure alignment of the coupling blocks, and swivel connectors for mounting in a tension test stand to insure a tensile test.

BRIEF DESCRIPTION OF THE DRAWINGS

FIG. 1 is a side elevation view illustrating a preferred embodiment of the invention in use;

FIG. 2 is a side elevation view in section taken on line 2—2 of FIG. 1;

FIG. 3 is a top view of a chip and substrate with the connector block of the present invention secured in place;

FIG. 4 is a perspective view of an alignment fixture; and

FIG. 5 is an end of the fixture of FIG. 4 shown in use.

DETAILED DESCRIPTION OF A PREFERRED EMBODIMENT

Referring to FIGS. 1 and 2 of the drawing, there is illustrated a preferred embodiment of a tensile connector block assembly in accordance with the invention shown in use. The connector block assembly is shown attached to a chip and a substrate for the application of an adhesion test force for testing the adhesion strength of the bond between the chip and the substrate.

The coupling assembly, as illustrated, comprises a pair of identical connector blocks 10 and 12 having a somewhat cubical or at least a square cross sectional configuration. The connector blocks may have any suitable cross sectional configuration, and preferably shaped to fit the chip. They may be round, square or rectangular.

The blocks are identical, and each has a generally square planar bonding surface or face 14 and 16, respectively, for bonding respectively to the surface of a chip 18 and to the surface of a substrate 20 to which the chip is bonded. The chip 18 is recessed into the surface of the substrate 20. The face of each block is perpendicular to the longitudinal axis of the block. This facilitates proper force alignment as will be explained.

Each of the connecting blocks has an outer connector end, with transverse connecting bores 22 and 24, respectively, for receiving pivot pins 40 and 42. These transverse bores provide pivoting connection that pivots about orthogonal axes that aids in proper force alignment as will become apparent.

The connecting or bonding face of each of the blocks is preferably substantially planar and smooth for maximum contact with the smooth planar face of a chip and a substrate. With this construction, the connector face of each of the blocks may be bonded directly to the face or surface of a chip or substrate with a low viscosity adhesive. This connection or bond directly to the face of the respective chip or substrate may be accomplished at room temperature using a cyanoacrylate adhesive. These adhesives are extremely strong and are available from one manufacturer under the trademark Superglue.

Another advantage of this adhesive is that it is dissolvable in acetone, thereby making the connector blocks reusable. The overall adhesive test connector assembly also includes pivoting swivel assembly in the form of a pair of clevises 26 and 28. The clevises or connector blocks 26 and 28 each respectively have a pair of spaced apart arms 30 and 32, 34 and 36 for receiving a connector block therebetween. The arms of the clevises include aligned pin receiving bores 22 and 24 for receiving a pin 40 and 42, respectively, for detachably connecting the respective clevises to the respective blocks 10 and 12.

Referring to FIG. 2, the clevises each are identical, and only the clevis 26 will be further described in detail. The clevis 26 includes a ball swivel assembly comprising a bore 44 having a spherical recess 46. A swivel pin having a semi-spherical head 48, and a threaded shank 50 extends through the bore 44. The spherical head 48 of the swivel pin 50 seats or rests in the spherical recess 46 at the inner end of the bore 44 of the clevis 26.

The combined pivot and swivel assembly assures a uniformly aligned force on the chip and substrate, perpendicular to the surface thereof attempting to separate them. As illustrated in FIG. 1, the assembly is used to apply a force along arrows 54 and 56 for testing the tensile adhesion strength of the bond between chip 18 and substrate 20. This force may be applied in a motorized test stand, such as those available from Ametek, Largo, Fla., such as under the trademark AccuForce Elite motorized test stand.

The connector assembly is precision aligned so that a pure tensile adhesion strength test is achieved. To accomplish this, the connector blocks 10 and 12 are axially aligned in a fixture as shown in FIG. 4. In the process of connecting or attaching the connector blocks to the chip and substrate, a fixture, as shown in FIG. 4, is utilized to assure alignment of the connector blocks.

In carrying out the steps of testing, the adhesion or bond strength test unit is selected, as shown in FIG. 3, wherein a chip 18 has been bonded to a substrate 20. A connector block 10 is selected and bonded directly to the center upper surface of the chip 18. Once the bond is set, the assembly is placed in the fixture of FIG. 4, with the substrate extending between the two grooved blocks, and the connector blocks 10 and 12 resting in the grooves in the fixture. The blocks 10 and 12 are preferably positioned so that the cross bores 22 and 24 for pins 40 and 42 are at a right angle to one another. With the block 10 bonded to the chip and in the fixture, the second block 12 is supported in the fixture in alignment with block 10 and bonded to the back face of the substrate 20.

Because of the aligned grooves 66 and 68, the block 12 will be aligned with the block 10. Thus, when the attachment of the connector assembly is established and placed in a test stand, the testing force will be directly perpendicular to the surfaces of the respective chip and substrate and along the longitudinal axis of the connector blocks. This assures a true adhesion test or tensile adhesion test as opposed to a peeling test as may occur with unaligned units.

Referring specifically to FIG. 4, a fixture block, designated generally at 58, has two interconnected support sections 60 and 62 separated to leave a space 64 therebetween for receiving the assembled chip and substrate. A pair of V-grooves 66 and 68 are aligned and designed to receive the connector blocks, and align them during bonding of the second of the blocks to the chip and substrate assembly. The fixture 58 can accommodate and align blocks that are either square or round. Blocks of different sizes may be aligned by using spacers 68 and 70 (or a single V-shaped spacer on one side), as shown in FIG. 4. A pair of round blocks would be accommodated and aligned as shown at 72 (in phantom) in FIG. 5. Spacers or shims can also be used to align different size round connector blocks.

The blocks may be selected to have any suitable cross-sectional size and configuration to cover most (preferably at least 60%) of the area of the chip to be tested. For example, different size blocks may be used and properly aligned by using spacers on the side of the smaller blocks. Round blocks can also be used and properly aligned in the illustrated fixture. With this arrangement, maximum connection and coverage of the chip is achieved.

The assembly, in accordance with the invention, because of its uniform application of force and more reliable and uniform connection, gives a true tensile test as opposed to a peel test. With this arrangement, bending of the ceramic substrate is eliminated, thus assuring a true tensile test. The cube or square surface of the block acts as an extender plate covering most of the die. The swivel assembly assures coaxial alignment of the forces. The results of tests with this structure has shown a tighter standard deviation. The range of failure types has narrowed to mostly material failures. The connector blocks can be reused, thus reducing costs of material and manufacturing.

While various preferred embodiments have been shown and described, including embodiments directed to both epoxy and metal-glass compositions, it should be understood that modifications and adaptations thereof will occur to persons skilled in the art. Therefore, the protection afforded the invention should not be limited except in accordance with the spirit of the following claims and their equivalents.

I claim:

1. A coupling assembly for coupling the surfaces of a semiconductor chip and its supporting carrier substrate to a tensile testing machine for testing the strength of a bond between the chip and the carrier substrate, comprising in combination:

a semiconductor chip and a substrate, said chip bonded to a supporting surface of said substrate, a pair of connector blocks, each having a bonding end, with a substantially planar bonding face for bonding to the surface of one of said chip and said substrate and a connector end with detachable connecting means for mounting in a tensile testing machine.

2. The coupling assembly of claim 1 wherein:
said chip and said carrier have oppositely directed substantially square faces; and
said connector block has a substantially square cross-section and central axis normal to said bonding face and said connector end includes a pin receiving bore transverse to said axis.

3. The coupling assembly of claim 2 further comprising a swivel assembly for connecting to said connector end for mounting in a tension test stand for testing the bond between said chip and said substrate.

4. The coupling assembly of claim 3 wherein said swivel assembly includes a clevis for connecting to said connector end and an elongated threaded member pivotally connected to said clevis for extending generally co-axially of said connector block.

5. The coupling assembly of claim 2 wherein said connector blocks are identical in cross sectional size and configuration for ease of alignment with one another in a jig.

6. The coupling assembly of claim 5 wherein said detachable connecting means comprises a swivel assembly for connecting to said connector end for mounting in a tension test stand for testing the bond between said chip and said substrate.

7. The coupling assembly of claim 6 wherein said swivel assembly includes a clevis for connecting to said connector end and an elongated threaded member pivotally connected to said clevis for extending generally co-axially of said connector block.

8. The coupling assembly of claim 1 wherein said connector blocks are identical in cross sectional size and configuration for ease of alignment with one another in a jig and have a length greater than a width thereof with a central axis normal to said bonding face and said connector end includes a pin receiving bore transverse to said axis.

9. The coupling assembly of claim 1 wherein said detachable connecting means comprises a swivel assembly including a clevis for connection to said connector end and an elongated threaded member pivotally connected to said clevis for extending generally co-axially of said connector block for mounting in a tension test stand for testing the bond between said chip and said substrate.

10. A connector assembly for connecting to opposite surfaces of a sandwich for testing the strength of an adhesive bond between a pair of surfaces, said connector assembly comprising in combination:
a semiconductor chip and a substrate, said semiconductor chip bonded to a surface of said substrate;
a pair of connector blocks for bonding to oppositely directed faces of said semiconductor chip and said substrate to which the chip is bonded, each connector block having a bonding end and a connector end; and
connecting means including a swivel assembly for connecting to said connector end for mounting in a tension test stand for testing the bond between said chip and said substrate.

11. The connector assembly of claim 10 wherein said connector blocks are identical in cross sectional size and configuration for ease of alignment with one another in a jig and each has a central axis normal to said bonding face, and said connector end includes a pin receiving bore transverse to said axis.

12. The connector assembly of claim 10 wherein said detachable connecting means comprises a swivel assembly for connecting to said connector end for mounting in a tension test stand for testing the bond between said chip and said substrate.

13. The connector assembly of claim 12 wherein said swivel assembly includes a clevis for connecting to said connector end and an elongated threaded member pivotally connected to said clevis for extending generally co-axially of said connector block.

14. The connector assembly of claim 10 wherein said connector blocks are identical in cross sectional size and configuration for ease of alignment with one another in a jig and have a length greater than a width thereof with a central axis normal to said bonding face and said connector end includes a pin receiving bore transverse to said axis.

15. A method for testing the tensile strength of a bond between a chip and a substrate, the steps comprising:
selecting a pair of connector blocks, each block having a substantially planar connecting face for bonding to oppositely directed faces of said chip and substrate, and a coupling end for mounting in a tensile testing machine;
bonding a connecting face of said pair of connector blocks to each one of said oppositely directed faces of said chip and substrate; and
applying a selected amount of aligned tension via said connector blocks to said chip and substrate.

16. A method for testing according to claim 15 wherein said step of selecting a pair of connector blocks includes selecting said blocks to be identical in cross sectional size and configuration for ease of alignment with one another in a fixture, selecting said blocks to have a length greater than a width thereof with a central axis normal to said bonding face and said connector end includes a pin receiving bore transverse to said axis.

17. A method for testing according to claim 16 wherein said step of applying said tension comprises:
selecting and connecting a swivel connector assembly to said coupling end; and
mounting said swivel connector assembly in a tensile testing machine.

18. A method for testing according to claim 17 wherein said step of bonding a connecting face of said pair of connector blocks to each one of said oppositely directed faces of said chip and substrate includes aligning said connector blocks in a fixture.

19. A method for testing according to claim 16 wherein said step of applying said tension comprises:
selecting and connecting a swivel connector assembly to said coupling end; and
mounting said swivel connector assembly in a tensile testing machine.

20. A method for testing according to claim 16 wherein said step of bonding a bonding face of said pair of connector blocks to each one of said oppositely directed faces of said chip and substrate includes aligning one connector block with the center of one of said chip and substrate and bonding said bonding face thereto by means of a cyanoacrylate adhesive;
supporting said one connector block and said chip and substrate in a first groove of an alignment fixture; and
supporting the other of said connector block in a second groove of an alignment fixture while bonding same to the other of said chip and substrate.

* * * * *